(12) United States Patent
Benje et al.

(10) Patent No.: US 7,579,509 B2
(45) Date of Patent: Aug. 25, 2009

(54) METHOD AND DEVICE FOR PRODUCING 1,2-DICHLORETHANE BY MEANS OF DIRECT CHLORINATION

(75) Inventors: Michael Benje, Darmstadt (DE); Harald Hafenscher, Kelkheim (DE)

(73) Assignees: Uhde GmbH, Dortmund (DE); Vinnolit GmbH & Co. KG, Burgkirchen (DE)

( * ) Notice: Subject to any disclaimer, the term of this patent is extended or adjusted under 35 U.S.C. 154(b) by 0 days.

(21) Appl. No.: 11/597,122

(22) PCT Filed: Jun. 15, 2005

(86) PCT No.: PCT/EP2005/006437

§ 371 (c)(1),
(2), (4) Date: Nov. 8, 2007

(87) PCT Pub. No.: WO2005/123635

PCT Pub. Date: Dec. 29, 2005

(65) Prior Publication Data

US 2008/0125613 A1 May 29, 2008

(30) Foreign Application Priority Data

Jun. 17, 2004 (DE) .................. 10 2004 029 147

(51) Int. Cl.
*C07C 17/02* (2006.01)
*C07C 17/093* (2006.01)
(52) U.S. Cl. .................. 570/247; 570/246; 570/252
(58) Field of Classification Search .................. 570/246, 570/247, 252
See application file for complete search history.

(56) References Cited

U.S. PATENT DOCUMENTS

| | | | |
|---|---|---|---|
| 4,554,392 A | 11/1985 | Leuck et al. |
| 4,783,564 A | 11/1988 | Piotrowski et al. |
| 5,177,233 A | 1/1993 | Schmidhammer et al. |
| 6,235,953 B1 | 5/2001 | Schwarzmaier et al. |
| 6,841,708 B1 | 1/2005 | Benje |
| 7,009,084 B2 | 3/2006 | Benje et al. |
| 2004/0116625 A1 | 6/2004 | Hottovy et al. |

FOREIGN PATENT DOCUMENTS

| | | |
|---|---|---|
| DE | 2 364 095 C2 | 7/1974 |
| DE | 199 10 964 A1 | 9/2000 |
| EP | 0 026 349 B1 | 4/1981 |
| EP | 0 412 016 A2 | 5/1985 |
| EP | 0 907 626 B1 | 1/2000 |
| GB | 1 410 420 A | 10/1975 |
| JP | 6-157365 A | 6/1994 |
| WO | WO 03/070673 A1 | 8/2003 |
| WO | WO 03/074167 A1 | 9/2003 |

*Primary Examiner*—Jafar Parsa
(74) *Attorney, Agent, or Firm*—Marshall & Melhorn, LLC

(57) ABSTRACT

The invention refers to a process for the production of high-purity 1,2-dichloroethane from dissolved chlorine and dissolved ethylene, which are brought into contact with each other in a circulating liquid reaction fluid, which mainly consists of 1,2-dichlorethane and a catalyst and flows through at least one vertically arranged loop-type reaction section, both legs of the loop being connected to an overhead degassing vessel from where the reaction product is withdrawn either in gaseous or in liquid state or in both gaseous and liquid state, and numerous admixing sections being arranged in the leg of the loop in which the liquid rises, and each of these admixing sections having one upstream feed point for dissolved or gaseous ethylene and one downstream feed point for dissolved chlorine and, if required, the admixing sections featuring static mixers.

2 Claims, 1 Drawing Sheet

METHOD AND DEVICE FOR PRODUCING 1,2-DICHLOROETHANE BY MEANS OF DIRECT CHLORINATION

BACKGROUND OF THE INVENTION

The invention relates to a process and a device for the production of 1,2-dichloroethane, hereinafter referred to as "EDC", which primarily serves as an intermediate product in the production of monomer vinyl chloride, hereinafter referred to as "VCM", which, in turn, is used to produce polyvinyl chloride (PVC). Hydrogen chloride HCl is obtained when EDC is reacted to produce VCM. Hence, the preferred method of producing EDC from ethylene $C_2H_4$ and chlorine $Cl_2$ is such that a balance is maintained between the hydrogen chloride HCl produced and consumed in the various reactions shown below:

$$Cl_2 + C_2H_4 \rightarrow C_2H_4Cl_2 \text{ (pure EDC)} + 218 \text{ kJ/Mole} \quad (1)$$

$$C_2H_4Cl_2 \text{ (crackable EDC)} \rightarrow C_2H_3Cl \text{ (VCM)} + HCl - 71 \text{ kJ/Mole} \quad (2)$$

$$C_2H_4 + 2\,HCl + \tfrac{1}{2}O_2 \rightarrow C_2H_4Cl_2 \text{ (raw EDC)} + H_2O + 238 \text{ kJ/Mole} \quad (3)$$

The process for the production of VCM with an adequate HCl balance, hereinafter referred to as "balanced VCM process", comprises the following process steps:

direct chlorination, in which one portion of the required EDC is produced from ethylene $C_2H_4$ and chlorine $Cl_2$ in the presence of a homogeneous catalyst and made available as so-called pure EDC;

oxychlorination, in which the remaining portion of the required EDC is produced from ethylene $C_2H_4$, hydrogen chloride HCl and oxygen $O_2$ and made available as so-called raw EDC;

fractionating EDC purification, in which the secondary products formed in the oxychlorination and EDC pyrolysis sections are removed from the raw EDC, the recycle EDC returned from the VCM fractionation section and, as an option, from the pure EDC in order to obtain a so-called feed EDC suitable for use in the EDC pyrolysis section; if desired, it is also possible to distil the pure EDC from the direct chlorination section in the heavy ends column of the EDC distillation section;

EDC pyrolysis, in which the feed EDC is thermally cracked; the mixture leaving the reactor is the cracked gas which consists of VCM, hydrogen chloride HCl and non-reacted EDC as well as secondary products;

VCM fractionation, in which the desired pure VCM product is separated from the cracked gas, while the other essential substances, viz. hydrogen chloride HCl and non-reacted EDC, contained in the cracked gas are recovered separately in the balanced VCM process and returned as recycle HCl or recycle EDC.

In most industrial-scale processes, a circulating stream of EDC reaction product is used as the reaction fluid in the direct chlorination section. The circulating stream can be generated in a loop-type reactor with external or internal circulation system. The circulating stream can also be generated in a system with forced or natural circulation. In most cases, ferric chloride is used as catalyst; in addition, sodium chloride, which can inhibit the formation of heavy ends, may be admixed as an additive.

The state of the art as regards direct chlorination is, for instance, described in DE 199 10 964 A1. The process according to DE 199 10 964 A1 aims at suppressing side reactions, especially the continuation of the chlorination process of EDC to 1,1,2-trichlorethane, by letting most of the chlorination reaction to take place in the homogeneous liquid phase. The ethylene, which is less readily soluble in EDC than chlorine, is completely dissolved in the main stream of the circulating EDC reaction fluid in a co-current bubble column. The chlorine, which is more readily soluble in EDC than ethylene, is dissolved in a super-cooled EDC part-stream and the resulting solution of chlorine in EDC is fed to the circulating main stream which already contains the dissolved ethylene.

Reaction (1) is usually run with a slight surplus of ethylene, in order to rule out corrosion problems in the reaction system, intensified formation of secondary products and problems involved in the treatment of chlorine-bearing waste gas streams. The reactor is supplied with a ratio-controlled feed of chlorine and ethylene, the ethylene content of the stream leaving the reactor serving as the control variable. The general aim for economical reasons is to minimise the surplus of ethylene at the reactor outlet in order to avoid excessive losses of ethylene.

It was further found that the formation of secondary products in reaction (1) was particularly low when running the reaction completely in the liquid phase, as also described in WO 03/070673 A1. To achieve this, it is required to make the ethylene dissolve completely in the reaction tube before the dissolved chlorine is added. The small gas bubbles initially produced by the gas feed device will grow along this section by coalescence and will finally reach a constant equilibrium variable resulting from coalescence and disintegration processes. This is an effect with a negative impact on the exchange of materials as the surface available for the exchange of fluids involved will become smaller as the bubble diameter becomes larger with a certain total volume of gas.

Reaction (1) in the subsequent reaction section, which is homogenous for the most part, proceeds kinetically according to a second-order velocity law. If both reactants initially have a stoichiometric ratio or if one reactant is in slight surplus, the reaction will proceed more slowly than it would if one reactant such as ethylene, for example, were initially present in a higher surplus in reaction (1). Transferred to a reactor of the type described herein, this means that the reaction is completed after a shorter run in the circulating reaction fluid stream than this would be the case with a lower initial surplus in ethylene.

The combination of the effects in ethylene dissolution, the reaction itself and at the commencement of boiling determines the dimensions of the reactor according to the conventional state of the art and makes it difficult to increase the capacity at a later stage.

The aim of the present invention, therefore, is to provide an economical process as well as a device which will permit an increase of the capacity without enlarging the external reactor dimensions while producing EDC of high purity.

BRIEF SUMMARY OF THE INVENTION

The aim can be achieved by:

a plurality of at least three admixing sections are arranged in the leg of the loop in which the liquid rises, each of these admixing sections has one upstream feed point for dissolved or gaseous ethylene and one downstream feed point for dissolved chlorine and may also have a static mixer.

Usually the feed point is designed as an injection nozzle, but it is also possible to choose a different design.

The provision of a plurality of reaction sections as defined by the admixing sections in the riser of the reactor loop described above results in the following advantage: By arranging the reaction sections in series, all the sections except the last can be operated with a high surplus in ethylene, which makes it possible to shorten the reaction sections considerably and this, in turn, allows several reaction sections to be arranged in a single reaction tube of economical size. In this way, it is possible to accomplish very high production capacities with a given reactor size. The non-reacted ethylene of the respective upstream reaction section is transferred in dissolved state to the next dissolving and reaction section. Apart from the last section, which precedes the reactor outlet, the ethylene/chlorine ratio in all reaction sections is preferably fixed. The ethylene/chorine ratio in the last reaction section, however, is controlled by the conventional method, the control variable being the ethylene content of the gas stream leaving the reactor.

Surprisingly, this results in the additional advantage that the ethylene losses, referred to the amount of EDC produced, decrease with an increasing number of reaction sections installed, i.e. with an increase in the EDC produced in a reactor loop of the type described herein. This is due to the fact that the only ethylene losses in the overall system are the losses in the last reaction section, there being no ethylene losses in the upstream reaction sections. As the reaction takes place in the liquid phase according to the process description given in WO 03/070673 A1, all the advantages of said system, especially the very low formation of secondary products even at relatively high reaction temperatures, are retained. Further shortening of the reaction sections can be achieved by combining the series arrangement of the reaction sections described above with an acceleration of the ethylene dissolution/reaction process by the installation of static mixing elements.

The installation of several ethylene feed points in the riser of the reactor loop will result in an increase of the mean gas content in the riser and, consequently, in the propellant force which is inevitably required to ensure natural circulation. This makes it possible to integrate static mixers in the appropriate reaction sections, the use of such mixers being basically known from EP 907 626 A1, but owing to the pressure losses incurred in other processes, they have to be operated with an energy-intensive recycling system, which has a detrimental effect on the economic efficiency of the process, and would adversely affect the control behaviour of a reactor loop with natural circulation, in particular the part-load performance.

A further embodiment of the invention provides for supplying a highly hyper-stoichiometric amount of ethylene at all ethylene feed points except that of the last downstream admixing section. Feeding a 10 to 20% hyper-stoichiometric amount of ethylene has proved to be economically very efficient. Although the increased feed will make it necessary to accordingly enlarge the respective dissolving section, it will accelerate the reaction as a whole, which will result in a reduction of the overall height and allow additional feed points to be installed and the conversion rate to be improved.

Considering all the above criteria it is possible to use this method to achieve at least double the conversion rate by reaction (1) with a boiling reactor of conventional size and reconstructed according to the invention. The great advantage of the invention is that revamping existing plants can easily be performed to achieve a capacity increase. It goes without saying that for economical reasons it is recommended, especially with regard to industrial-scale plants, to equip boiling reactors with the feed devices according to the present invention as early as at the outset of the original planning phase.

The boiling reactor according to the present invention is characterised by an excellent part-load performance, as it is possible to deactivate individual feed points even during operation, which is another advantage of the present invention. It is expedient to deactivate the upper feed points first and to lower the pressure so that the produced EDC can boil earlier. It is thus possible—even at low conversion rates—to compensate for the pressure loss caused by static mixers, if provided.

The invention also refers to a device for implementing the process with a boiling reactor which consists of a degassing vessel, a reaction loop with natural circulation as well as discharge devices for the EDC produced and at least two feed devices each for dissolved chlorine and ethylene. The device may optionally also include static mixers.

BRIEF DESCRIPTION OF THE DRAWINGS

The invention is illustrated in more detail by means of the following example.

DETAILED DESCRIPTION OF THE INVENTION

Figure 1:
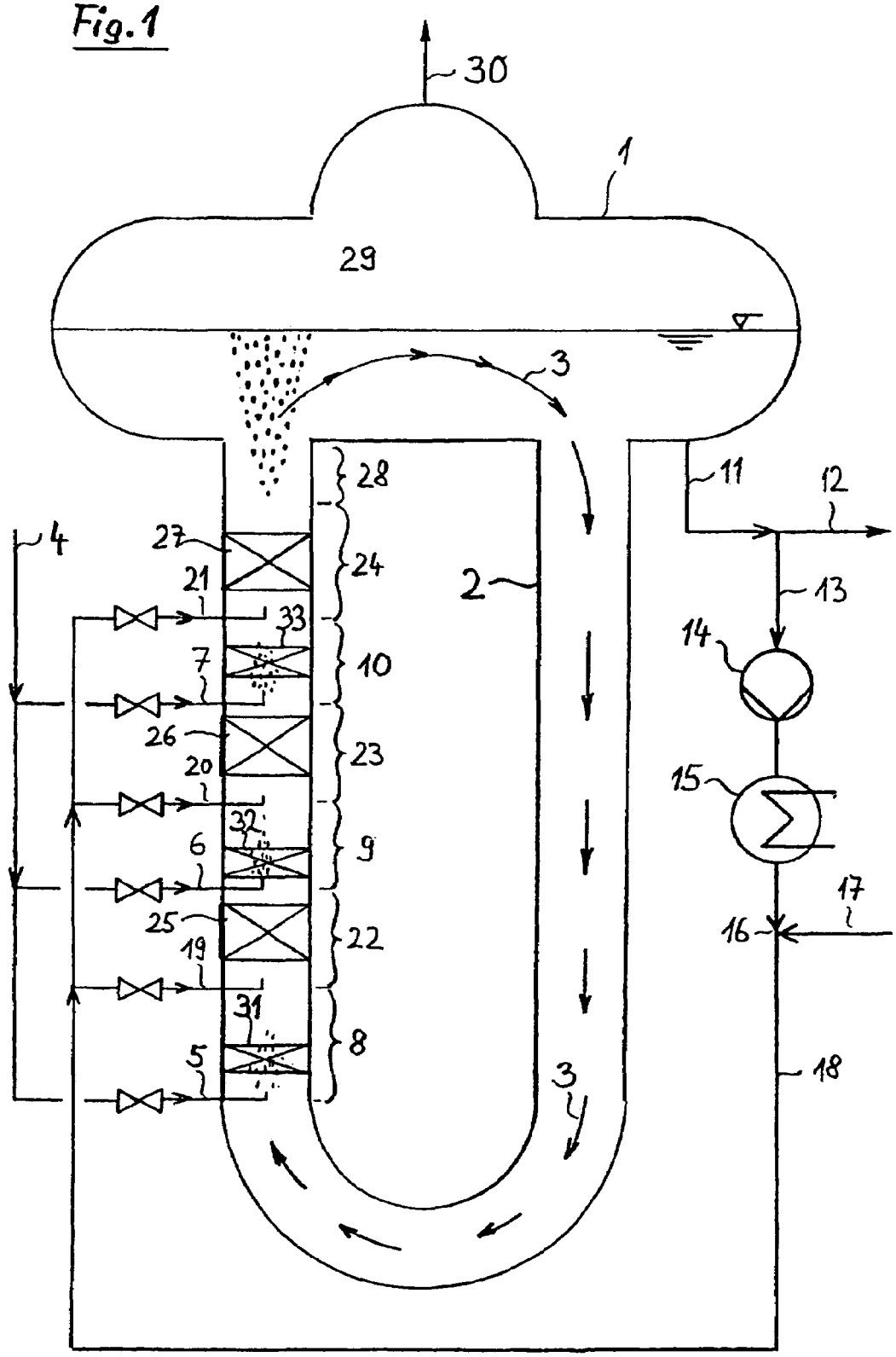
FIG. 1 shows a direct chlorination reactor consisting of degassing vessel 1 and loop 2 in which liquid EDC 3, indicated by arrows, is circulated and which serves to run reaction (1), as well as the feed points for chlorine and ethylene according to the present invention.

Gaseous pressurised ethylene 4 is distributed via control valves to ethylene feed points 5, 6 and 7. The ethylene feed points are designed so to produce fine bubbles, symbolically represented by dots in FIG. 1, which can easily dissolve in the dissolving sections 8, 9 and 10. The dissolving sections 8, 9 and 10 may optionally be equipped with static mixers 31, 32 and 33.

The chlorine to be added is first dissolved in EDC. Part-stream 11 of the produced EDC is withdrawn from degassing vessel 1 and split into EDC stream 12, which may also be an intermittent bleed stream, and solution stream 13. Solution stream 13 is transferred by pump 14 to cooler 15 and subsequently to chlorine admixture point 16 where the gaseous chlorine 17 is added. Chlorine solution 18 is distributed at a controlled rate to chlorine feed points 19, 20 and 21 and injected into loop 2 via a nozzle which produces the maximum possible turbulence.

Reaction sections 22, 23 and 24 which serve to run reaction (1) in the pure liquid phase are arranged downstream of chlorine feed points 19, 20 and 21. To improve the mixing quality, reaction sections 22, 23 and 24 are equipped with static mixers 25, 26 and 27.

In the upper area of loop 2, reaction section 24 is followed by boiling section 28, which is illustrated by bubbles in FIG. 1. The vaporous EDC degasses into vapour chamber 29 of degassing vessel 1 from where it is discharged as vaporous EDC product 30.

The invention is described in even more detail on the basis of a calculated example. Liquid EDC 3 is circulated at a rate of 8000 t/h in reaction loop 2 at a temperature of 90 to 135° C. Gaseous ethylene is fed to the loop via feed point 5 at a rate of 8892 kg/h, equivalent to 317 kmole/h, which dissolves in dissolving section 8 in the circulating EDC 3.

Liquid EDC (stream 13) is withdrawn at a rate of 1140 t/h from degassing vessel 1, pumped through heat exchanger 15 by means of pump 14, thereby being cooled to a temperature of between 30 and 60° C. At chlorine admixing point 16, gaseous or liquid chlorine is admixed to the cooled EDC stream at a rate of 61260 kg/h, equivalent to 864 kmole/h. The chlorine solution 18 thus obtained is split into three equal part-streams, each consisting of 380 t/h EDC and 20420 kg/h chlorine, equivalent to 288 kmole/h chlorine. These three part-streams are fed into the reactor loop via feed points 19, 20 and 21.

Alternatively (not illustrated in FIG. 1), the cooled EDC stream of 1140 t/h is first split into three equal part-streams of 380 t/h each, and 20420 kg/h, equivalent to 288 kmole/h, gaseous or liquid chlorine is admixed to each of these part-streams via separate chlorine admixing points. In this case, too, three part-streams of a solution of chlorine in EDC are obtained, each consisting of 380 t/h EDC and 20420 kg/h chlorine and which are fed into reactor loop 2 via feed points 19, 20 and 21.

The first ethylene stream 5, as seen from bottom to top in the riser of the reactor loop, which has dissolved in section 8 in the circulating EDC stream 3, is mixed with part-stream 19 of the chlorine-in-EDC solution. The reactants chlorine and ethylene react in the liquid phase along reaction section 22, whereby EDC is formed. As the dissolved ethylene is present at a molar surplus of 10%, the reaction of the dissolved chlorine in fact proceeds more rapidly than if the reactants were present in equimolar quantities or if ethylene were only present with a small surplus. The reaction heat causes the circulating EDC 3 temperature to rise. As the temperature of the admixed chlorine solution is markedly lower than that of the circulating EDC 3, part of the reaction heat is dissipated as a result of heating the chlorine solution to the temperature level of the reactor contents. Hence, this method and the appropriate setting of the reactor pressure permit boiling in the lower reaction zones and, consequently, an increased production of by-products, can be suppressed.

When the reaction of the dissolved chlorine is completed, the circulating EDC 3 which now enters the second ethylene dissolving section 9, as seen from bottom to top in the riser of the reactor loop, will contain already dissolved ethylene. Dissolved ethylene is transferred at a rate, of 814 kg/h, equivalent to 29 kmole/h, with the EDC 3 into the ethylene dissolving section 9. Next, gaseous ethylene is fed via ethylene feed point 6 into the dissolving section at a rate of 8078 kg/h, equivalent to 288 kmole/h, which dissolves in the circulating EDC 3 along the ethylene dissolving section 9. At the end of ethylene dissolving section 9, 8892 kg/h equivalent to 317 kmole/h dissolved ethylene is again contained in EDC 3.

Analogously, part-stream 20 of chlorine dissolved in EDC is added to, and the chlorine and ethylene react to form EDC, along reaction section 23. In this case, too, boiling of the reaction mixture is suppressed by the cooling action of the cooled chlorine solution stream and by an appropriate setting of the reactor pressure. Owing to the molar surplus of ethylene of 10%, the chlorine likewise reacts rapidly.

In view of the fact that ethylene losses and an excessive content of dissolved ethylene in the EDC produced constitute a disadvantage from the economic point of view and are, indeed, undesirable in the downstream process sections, the last, i.e. the uppermost, reaction section is operated with only a small ethylene surplus.

In the same way as downstream of the first reaction section, dissolved ethylene is transferred at a rate of 814 kg/h, equivalent to 29 kmole/h, into the ethylene dissolving section 10. Gaseous ethylene is fed via ethylene feed point 7 into the dissolving section at a rate of 7289 kg/h, equivalent to 260 kmole/h, which dissolves in the circulating EDC along the ethylene dissolving section 10.

Subsequently, part-stream 21 of chlorine dissolved in EDC is added. The ethylene is now present with a molar surplus of only 0.35%, as a result of which reaction section 24 will be considerably longer than reaction sections 22 and 23. After passing through reaction section 24, the hydrostatic pressure will decrease to an extent that the reaction mixture will start to boil and the reaction product can be withdrawn in gaseous state from degassing vessel 1.

LEGEND

1 Degassing vessel
2 Loop
3 Liquid EDC
4 Ethylene
5 Ethylene feed point
6 Ethylene feed point
7 Ethylene feed point
8 Dissolving section
9 Dissolving section
710 Dissolving section
11 Part-stream
12 EDC stream
13 Solution stream
14 Pump
15 Cooler
16 Chlorine admixture
17 Gaseous chlorine
18 Chlorine solution
19 Chlorine feed point
20 Chlorine feed point
21 Chlorine feed point
22 Reaction section
23 Reaction section
24 Reaction section
25 Static mixer
26 Static mixer
27 Static mixer
28 Boiling section
29 Vapour chamber
30 Vaporous EDC product
31 Static mixer
32 Static mixer
33 Static mixer

The invention claimed is:

1. A process for the production of 1,2-dichloroethane of high purity from dissolved chlorine and dissolved ethylene, which are brought into contact with each other in a circulating liquid reaction fluid, which mainly consists of 1,2-dichloroethane and a catalyst and which flows through at least one vertically arranged loop-type reaction section, both legs of the loop being connected to a degassing vessel arranged at the top, from which the reaction product is withdrawn either in gaseous or in liquid state or in both gaseous and liquid state, wherein
   a plurality of at least three admixing sections are arranged in the leg of the loop in which the liquid rises,
   each of these admixing sections has one upstream feed point for dissolved or gaseous ethylene and one downstream feed point for dissolved chlorine and may further have static mixers.

2. A process according to claim 1, wherein a highly hyperstoichiometric amount of ethylene is fed to all ethylene feed points except that of the last downstream admixing section.

* * * * *